United States Patent [19]

Long

[11] Patent Number: 5,306,274
[45] Date of Patent: Apr. 26, 1994

[54] LASER-POWERED HIGH TEMPERATURE ENERGY DELIVERY TIP ELEMENT WITH THROUGHFLOW OF VAPORIZED MATERIALS AND ELECTROCAUTERIZATION CAPABILITY

[75] Inventor: Gary Long, Cincinnati, Ohio

[73] Assignee: Laser Centers of America, Cincinnati, Ohio

[21] Appl. No.: 958,836

[22] Filed: Oct. 9, 1992

Related U.S. Application Data

[63] Continuation-in-part of Ser. No. 812,449, Dec. 23, 1991.

[51] Int. Cl.$^5$ ............................................. A61B 17/36
[52] U.S. Cl. ....................................... 606/28; 606/15; 606/16; 606/27
[58] Field of Search ................... 606/27, 28, 29, 7, 15, 606/16, 37, 38, 39, 40, 45, 46

[56] References Cited

U.S. PATENT DOCUMENTS

| | | | |
|---|---|---|---|
| 3,595,239 | 7/1971 | Petersen | 606/45 |
| 4,592,353 | 6/1986 | Daikuzono | 606/16 |
| 4,676,242 | 6/1987 | Doi | 606/16 |
| 4,832,024 | 5/1989 | Boussignac et al. | 606/15 |
| 4,959,063 | 9/1990 | Kojima | 606/15 |
| 5,061,265 | 10/1991 | Abela et al. | 606/7 |
| 5,071,222 | 12/1991 | Laakmann | 606/27 X |
| 5,078,712 | 1/1992 | Easley et al. | 606/16 |

*Primary Examiner*—Peter A. Aschenbrenner
*Attorney, Agent, or Firm*—Lowe, Price, LeBlanc & Becker

[57] ABSTRACT

A tip element is provided for attachment to a small hand-held elongate surgical tool, to enable a surgeon to utilize laser light energy conveyed along a single optical fiber and converted at a fine point of the tip element into a high temperature energy flux. Thus, instead of emitting laser light energy directly to a patient's tissues, the surgeon applies an extremely hot pointed tip very precisely to generate such high local temperatures as to substantially vaporize or gasify the tissue. An annulus is defined adjacent to and immediately around the heated portion of the tip element so that vapors and gaseous products generated during use of the device are immediately removed from the surgical site. An electrical connection may be provided to a distal portion of the tip element close to its heated point to enable a surgeon to contact a bleeding blood vessel thereby to effect cauterization by a cauterization current driven through the patient's body and controlled by a foot-operated switch.

31 Claims, 2 Drawing Sheets

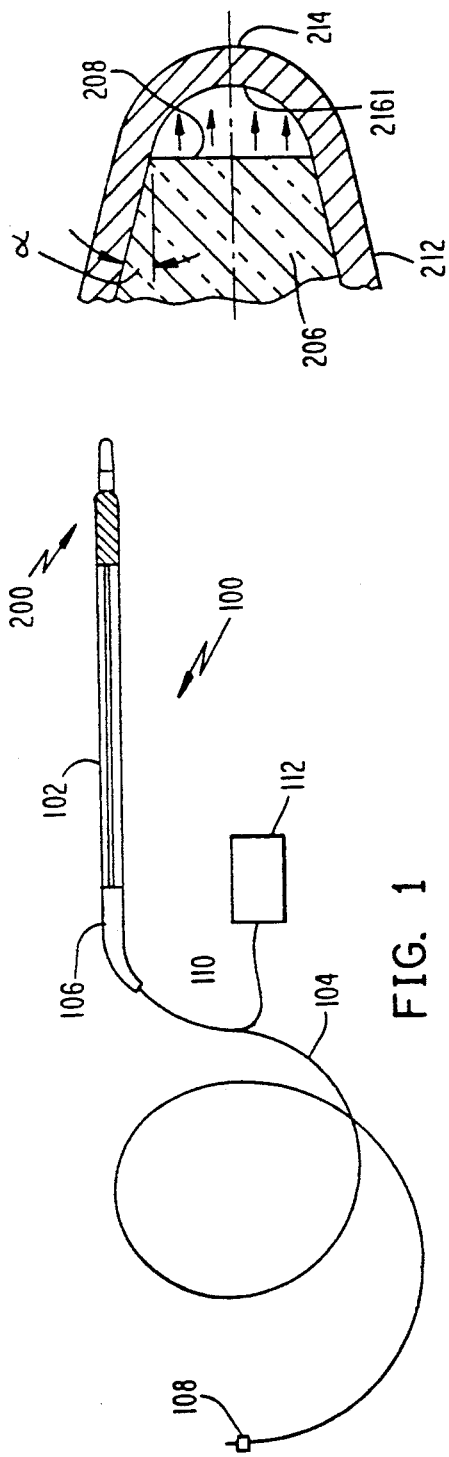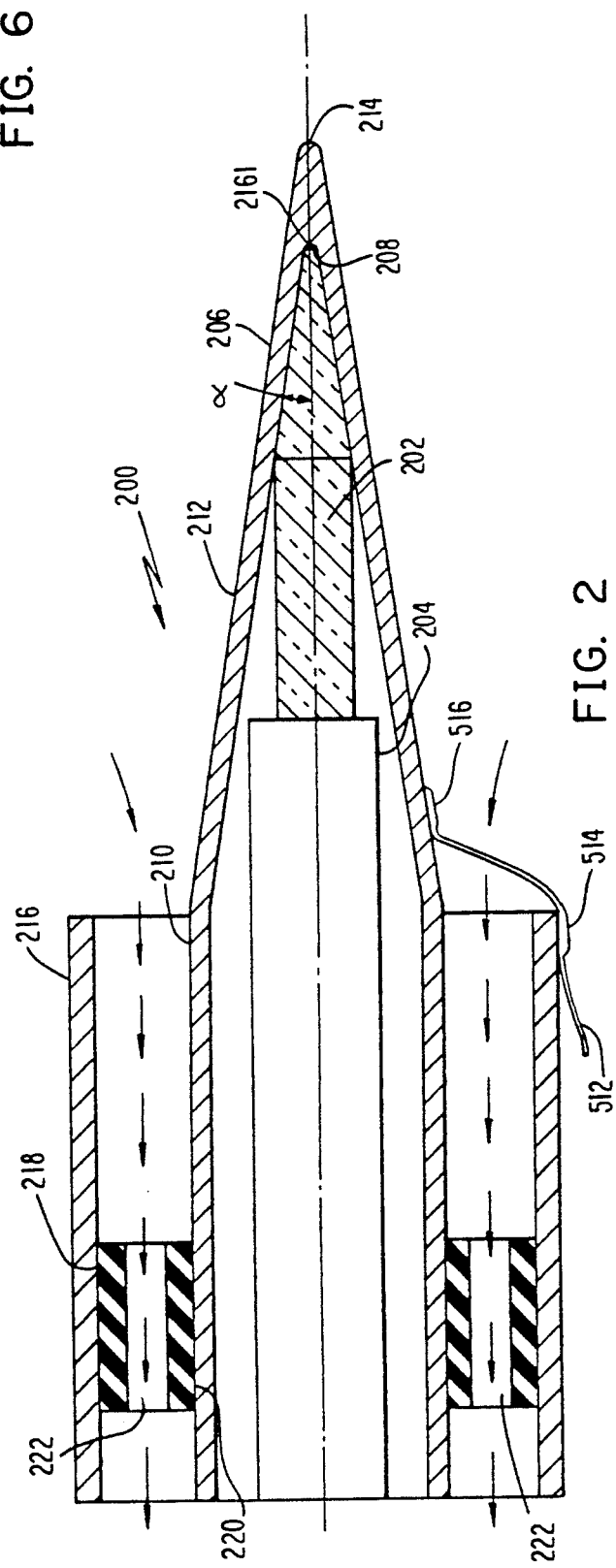

LASER-POWERED HIGH TEMPERATURE ENERGY DELIVERY TIP ELEMENT WITH THROUGHFLOW OF VAPORIZED MATERIALS AND ELECTROCAUTERIZATION CAPABILITY

This is a Continuation-In-Part of copending U.S. application Ser. No. 07/812,449 filed Dec. 23, 1991.

FIELD OF THE INVENTION

This invention relates to a tip element for converting laser energy for high temperature localized application of heat, and more particularly to a tip element that facilitates immediate removal of gaseous and/or vaporized substances produced by the application of energy at a very high temperature to perform surgical functions and with the capability of providing electrocauterization of incised blood vessels.

BACKGROUND OF THE PRIOR ART

Many laser surgical systems are known in which a hand-held surgical device is applied by a surgeon to deliver energy to locally heat tissues to such a high temperature that they disintegrate into gaseous and/or vaporized substances. Such a delivery of energy, to effect localized incisions, requires a small tip element shaped and oriented to enable the surgeon to see clearly where the energy is being applied. Although the tip element must be finely formed to allow precise surgery it must be rugged enough for prolonged use, i e., it should not need to be replaced frequently during surgery on a particular patient.

It is inevitable in surgery that blood vessels are occasionally incised, whether the surgeon is applying a scalpel or any other surgical tool. To prevent undesirable bleeding from a cut blood vessel, the surgeon or an assistant typically cauterizes the incised blood vessel as quickly as possible. Such cauterization may require separate tools, but certain versatile laser energy delivering tip elements are also known which enable a user to selectively apply the same tool to effect either incisions or cauterization of incised vessels. One example is disclosed in copending U.S. application Ser. No. 07/812,449 of which this application is a Continuation-In-Part. Pertinent aspects of that application are incorporated herein by reference.

Regardless of how good the local ventilation is in an operating room, a surgeon performing precise incision/cauterization with a surgical tool generating a high temperature locally must contend with the presence of unpleasant odors, smoke and the gaseous and/or vaporized byproducts of the heated tissues every time he or she applies energy. Surgeons and their operating room assistants would experience less stress and be able to function more efficiently if the gaseous and/or vaporized substances produced during such surgery and cauterization were immediately removed from the site where they are produced.

A need, therefore, clearly exists for a rugged high temperature energy delivery tip element which enables a user to remove gaseous and/or vaporized substances immediately upon their production during surgery and cauterization.

Furthermore, even though versatile energy delivery tip elements are known which are useful for both incision making and for cauterization, to simplify the surgeon's task in operating the hand-held laser surgical tool, it is also highly desirable to provide a separately operated cauterization system in which controlled amounts of heat can be selectively delivered by the incision-making tip element itself without the need for separate tools or additional hand-operated actuation elements.

The present invention, as described more fully hereinbelow and as illustrated in the accompanying figures, is intended to meet both of these needs, i.e., to immediately remove gaseous and/or vaporized substances from the surgical site and, with the same tip element, to enable the surgeon to selectively deliver via the same tip element an electrocauterization controlled by a foot-actuated control.

SUMMARY OF THE INVENTION

Accordingly, it is a principal object of this invention to provide a rugged high temperature energy delivery tip element suitable for use in a hand-held surgical tool to precisely deliver energy to perform surgical incisions while, simultaneously, facilitating the immediate removal of gaseous and/or vaporized substances generated by the application of energy.

It is another object of this invention to provide a finely shaped but rugged energy delivery tip element by which a surgeon can apply energy precisely and be able to clearly view the site of such energy application by the immediate removal through the same tip element of any gaseous and/or vaporized substances generated during use of the tip element.

It is yet another object of this invention to provide an energy delivery tip element which, by the selection of an appropriately sized and shaped single optical fiber, facilitates the delivery of sufficient laser energy to make precise incisions in an easily viewed manner by generating a very high local temperature while simultaneously removing any gaseous and/or vaporized substances generated during its use.

It is a related further object of this invention to provide an inexpensive and simple energy delivery tip element by which a surgeon can apply laser energy in the form of locally applicable high temperature heat at a rate suitable for cutting through tissues while simultaneously removing from the surgical site any gaseous and/or vaporized substances generated during the operation and, furthermore, enabling the surgeon to utilize the same tip element to deliver a separately controlled electrocauterization current to cauterize and seal off incised blood vessels quickly and efficiently.

These and other related objects are realized by providing, in a preferred embodiment, a tip element for precisely applying energy at a high local temperature, wherein the tip element includes an optical fiber having an extended conically shaped distal end portion formed into a conical shape with an end face for emitting a flux of laser energy, and a matchingly shaped fine conical cover element comprising a second material formed and positioned with respect to the distal end of the laser energy delivering optical fiber so as to intercept all of the emitted laser energy therefrom to heat a heat-applying first portion of the cover element and the heat-applying first portion of the cover element is formed as a closed cone, and the conically-shaped extended distal end portion of the optical fiber is correspondingly shaped and fitted to an inside surface of the cone.

In another aspect of this invention, the conical element is connected to a separately actuable electrical power source to apply a controlled electrocauterization current to cauterize severed blood vessels while suction is simultaneously applied immediately around the conical element to remove from the cauterization site any gaseous and/or vaporized substances generated by application of the cauterizing electrical current.

In another aspect of this invention, there is provided a method for controllably applying through a heated single needle-like fine conical tip sufficient laser energy converted to a high temperature heat flux for cutting through tissues, a controlled electrical current to perform electrocautery and, simultaneously, removing gaseous and/or vaporized substances during such surgical activity.

These and other related objects and aspects of the invention are realized in embodiments more fully described with reference to the accompanying drawings.

BRIEF DESCRIPTION OF THE DRAWINGS

FIG. 1 is a schematic view of a known structure by which laser energy is conveyed from a laser energy source through a hand-held tool to a laser energy delivery tip element.

FIG. 2 is a longitudinal cross-sectional view of a high temperature energy delivery tip element according to a preferred embodiment of this invention.

FIG. 6 is an enlarged partial cross-sectional view of the end of the tip element.

DETAILED DESCRIPTION OF THE PREFERRED EMBODIMENTS

Figures 3, 4, 5:
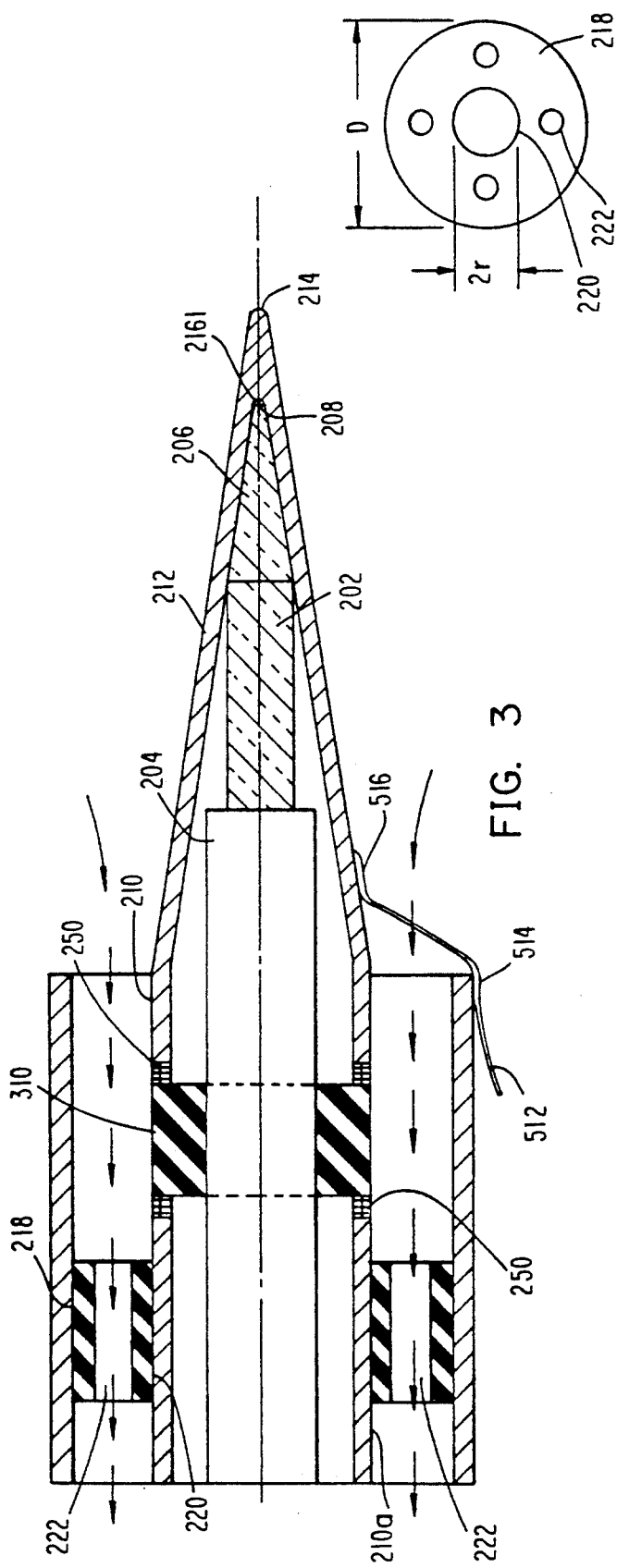
FIG. 3 is a longitudinal cross-sectional view of another embodiment of this invention.
FIG. 4 is a plan view of a spacer element included in the preferred embodiment per FIG. 2 to support and locate a single optical fiber to convey laser energy and, simultaneously, to facilitate the application of suction to withdraw from the surgical site any gaseous and/or vaporized substances generated during use.
FIG. 5 is a schematic illustration of a circuit arrangement by which a foot-controlled cauterization current may be provided to the tip element.

A surgeon applying laser energy for surgical purposes, e.g., for making incisions through a patient's tissues, typically holds in his or her hand a lightweight, tool 100 into which is fitted an elongate assembly having a specifically shaped energized tip element to apply heat by locally contacting body tissues. As best understood with reference to FIG. 1, such a hand-held surgical tool 100 typically has a slim elongate body 102 connected to a flexible element 104 at a junction 106. The flexible element 104, for example in known laser systems, typically comprises an outer tubular sheath protectively containing at least a suitable length of an optic fiber connected by a known junction 108 at one end to a source of laser light energy (not shown). In this manner, laser light energy of a suitable wavelength is received at junction 108 from a laser light source located at a convenient distance from the patient, and is conveyed via an optic fiber through flexible element 104, junction 106, and tubular element 102 to an energy applying tip element 200 of the hand-held surgical tool 100.

Laser energy delivery systems, particularly for medical applications in which different types of tissues are encountered, are becoming more and more application-specific. Different wavelengths of laser light can be applied to obtain correspondingly different effects on any given tissue. Similarly, when faced with a need to use laser light energy of a different wavelength, e.g., in order to cut through a different type of tissue such as muscle or bone, at least with known systems the surgeon needs to use different laser surgical tools specifically designed to deliver laser energy at the selected wavelength.

There are, however, many applications where it is required only that a very high local temperature be generated, sufficient to essentially vaporize a variety of tissues, and that a sufficiently large local energy flux be available to do so in a precise manner. The actual emission a laser light energy flux from the tip element is not always desirable and may thus be avoided.

For practical reasons, a single optical fiber is often employed to deliver the laser light energy from a laser energy source to and through the surgical tool to the tip element which is of small dimensions but of a precisely selected shape. Typically, such a single optical fiber must transmit a substantial amount of the received laser energy, e.g., over 85%. There are certain inherent limitations when laser light energy is thus delivered through a single fiber. Thus, if a certain power density of delivered laser energy is required to obtain a specific effect on tissue, then only the end surface of the fiber can be used to emit the energy.

The present invention, as described more fully hereinbelow, provides a practical means of transducing laser light energy into a corresponding high temperature heat flux regardless of the wavelength of the laser light energy being employed or the tissue treated thereby. It is ideally suited to use with single optical fibers delivering significant amounts of laser energy.

As will be appreciated, the application of a high temperature energy flux to a patient's tissues during a surgical procedure will cause disintegration of the tissue and generate vaporized or gaseous products. Under certain circumstances, this may interfere with the surgeon's view of the surgical site or may otherwise irritate the surgeon due to acrid smells. It is, therefore, highly desirable to provide suction immediately around the hottest portion of the tip element so that the vaporized or gaseous products are immediately removed to allow the surgeon unimpeded viewing and access to the surgical site. Such suction is most conveniently applied via a suction line 110 connected to any known means 112 for applying controlled suction therethrough. See FIG. 1. Suction line 110 may be carried for part of its length inside the outer tubular sheath of flexible element 104 which protectively contains the optic fiber. In effect, then, suction generated by suction means 112 is applied via suction line 110 through the elongate body 102 all the way to the tip element 200 where its availability is utilized in manner to be more fully described hereinbelow.

FIG. 2 is a longitudinal cross-sectional view of a preferred embodiment of the present invention, namely a tip element 200 conveniently mountable to the end of a hand-held slim elongate body 102 of a surgical tool 100. Tip element 200, in the form illustrated in FIG. 2, comprises a number of generally cylindrical elements disposed coaxially about an axis of symmetry X—X in cooperative manner. It should be understood that other geometries, within the spirit of the following description and as claimed herein, may be considered more desirable for accomplishing the same function in the same way in particular application. The tip element may be mounted to hand-held tool 102 in any known manner.

Along the axis X—X is provided an optical fiber 202 of the type typically provided with a protective cladding 204, of which an end portion is removed from optical fiber 202. The extreme distal end of optical fiber 202 is formed, by any conventional means, into a conical length 206 suspending a half-cone angle "α". The extreme end face of optic fiber 202 thus provides a small circular end face 208, normal to axis X—X, through which laser light energy transmitted along optic fiber 202 is emitted. As will be understood, a merely cantilevered end of a single optic fiber on its own would be quite fragile and would not last very long in use.

A length of a small-bore, thin-walled, cylindrical, strong metal tubing 210, having an internal diameter larger than an outer diameter of cladding 204 is swaged at one end to the form of a conical-walled portion 212 which is sealed and closed off, e.g., by welding, at a finely-pointed end 214. The half-cone angle of at least the inside surface of conical portion 212 is selected to be "α", namely the same as the half-cone angle of the extreme distal conically-formed end portion 206 of optic fiber 202. Any known techniques for swaging a thin-walled metal tube, and for sealing its end, may be utilized for this purpose.

Given the structural parameters discussed in the immediately preceding paragraphs, it becomes possible to insert the conical end portion 206 of optic fiber 202 in a tight matching fit into the conical space formed inside conical metal tubing portion 212. Laser energy emitting end face 208 thus emits laser energy directly to a correspondingly small portion of the inside metal surface, identified by the numeral 216 at the axis X—X and just inboard of pointed end 214. See also the enlarged view per FIG. 6.

It will be readily understood by persons of ordinary skill in the art how laser energy conveyed along optic fiber 202 is thus conveyed to be emitted from end face 208 to be entirely absorbed by the small mass of metal essentially forming the fine point 214 of the swaged metal tubing 210. This laser energy is absorbed by the small amount of metal there and point 214 becomes extremely hot, in fact so hot that it can be very precisely applied to tissue, e.g., a tumor, muscle, cartilage or even bone, to cause virtually instantaneous vaporization or gasification of the tissue thus contacted. It is, therefore, made easy for the surgeon-user manipulating such a fine and very hot point 214 to make precise incisions, to destroy undesirable tissue, and at sufficiently low power fluxes even to cauterize blood vessels or coagulate blood even with the tip element powered solely by the received/emitted laser energy.

Naturally, the application of intense heat to organic tissue will cause the immediate production of oxygenous gases and vapors as well as smoke from carbonization of the burned tissues. The oxygenous gases and vapors, the unpleasant smells, and smoke, can only irritate and distract the surgeon-user. It is, therefore, highly desirable to provide suction immediately around the heated tip portion of the device to promptly remove such gases and vapors.

As shown in FIG. 2, there is provided for this purpose a length of an outer tubing 216 coaxially about axis X—X. The open distal end of outer tubing 216 is preferably located close to the point at which cylindrical tubing 210 becomes conical portion 212.

To maintain a suitable relationship between outer tubing 216 and inner metal tubing 210, there is provided inside of tubing 216 and close to a forward distal end thereof a disc-like locator element 218 formed to have a central hole 220 sized to closely receive therethrough inner metal tubing 210 which has a diameter "2r". As best seen in plan view in FIG. 4, locator element 218 has an outer diameter "D" sized so as to be closely received inside outer tubing 216. Locator element 218 is also provided with a plurality of through apertures 222. The number and diameters of apertures 222 are selected to ensure a sufficient flow area through which gaseous and/or vaporized substances, inevitably mixed in with some ambient air, are sucked away at a satisfactory rate through the annular space defined between the outer surface of inner tubing 210 (of diameter "2r") and the coaxial inner cylindrical surface of outer tubing 216 (of diameter "D"). This is accomplished by communicating suction line 110, through slim elongate hand-held body 102 of surgical tool 100, by the action of suction means 112.

As noted earlier, it is a principal objective of this invention to provide a rugged surgical tip element for satisfactory prolonged use at low cost.

It is, therefore, necessary to carefully select the materials of which the above-described coacting elements are made. It is considered that the preferred material for optic fiber 202 is quartz, although other materials may be employed depending on the anticipated demands to be made on the device. Experience shows that quartz is a highly durable material capable of providing effective service under very high temperatures.

The tubing 210 is preferably made of a strong metal that can be given a clean, smooth finish and which is highly compatible with body tissue. Stainless steel and titanium are considered to be two highly suitable materials for this purpose, although other materials may be used instead for specific applications. Both stainless steel and titanium can be worked, i.e., swaged into a conical form of predetermined half-cone angle, and sealed by known techniques. Also, both of these metals demonstrate considerable physical strength at high temperatures even for relatively small-bore and thin-walled tubing. They are, therefore, regarded as particularly suitable for the present device.

Outer tubing 216, like inner tubing 210, is of relatively small bore and small wall thickness. Both stainless steel and titanium are considered suitable materials for forming outer tubing 216, although stainless steel may in practice prove to be less expensive yet fully capable of meeting all of the criteria for acceptability, e.g., low cost availability, smooth outer surface in commercially available tubing stock, compatibility with human tissue, and the like.

Locator element 218 is made of a material which is at least an electrical insulator and is preferably also a poor conductor of heat. It is considered that glass and known ceramics materials are suitable for forming locator element 218, although the latter may be easier to form with the plurality of apertures 222 to provide passages for the suction of gases and vapors as described earlier. What is important is that locator element 218 be long enough axially to be securely located inside outer tubing 216 to firmly support inner tubing 210. It is expected that there will be some forces applied during assembly of the tip element, and all the heated elements must be able to withstand the high temperature cycling and rigors of the anticipated working conditions during use of the surgical tool. Naturally, an adequate factor of safety must also be allowed. It is considered that the preferred materials quality fully.

It is considered that a convenient fiber core diameter of the order of 0.04 in. (approx. 1 mm.) should suffice for conveying an adequate flux of laser light energy for most surgical applications with the present invention. It is also considered that, for such a fiber, stainless steel or titanium tubing 210 having an outer diameter of about 0.08 in. (approx. 2 mm.) with a wall thickness of 0.006 in. (approx. 0.15 mm.) would be most suitable. Since the actual incision will occur at the finely pointed end 214 of the swaged and sealed inner tubing 210, that has a value for half-cone angle "α" of about 10°-20°, outer tubing 216 may conveniently have a diameter about twice the diameter of inner tubing 210 with approximately the same wall thickness. Persons of ordinary skill in the art can be expected to make comparable choices of size and proportion to suit particular needs.

With the structure described above, it should be expected that although some heat will be conducted along the conical portion 212 away from the hot metal tip 214. The provision of a thermally non-conductive locator element 222, coupled with the cooling incidental to flow of gases, vapors and ambient air through the annulus between inner tubing 210 and outer tubing 216, should keep outer tubing 216 cool enough so that contact with it will not adversely affect tissues close to the site of the surgical operation being performed with the tip element. In other words, it is expected that some contact will occur between the outer surface of outer tubing 216 and the tissue of the patient being operated by the surgeon. It is intended that such contacts, which are inevitable, should have no undesirable effect on the tissues contacted. The combination of flow through the annulus and interference to conductive heat transfer due to the nature of the material of locator element 218 should ensure this. Note that in FIG. 2 sequential arrows 224,224 indicate the direction of flow of air, gas and vapors induced by applied suction.

As noted earlier, the making of incisions in tissues, particularly soft body tissue, inevitably involves the cutting of blood vessels. Seepage of blood from such incised blood vessels may be stopped by either the surgeon or an assistant promptly cauterizing the cut ends of the vessel. This is a very common practice but, when the operation is performed in a very confined zone, e.g., in a patient's sinuses, it is highly desirable to enable the surgeon to effect cauterization selectively without changing the surgical tool and independently of assistance from others.

Recent developments in the field of electrocautery involves the application of a controlled electrical current to an inside blood vessel to generate localized heating of a sufficient magnitude to promptly cauterize the vessel. The cauterizing current enters the patient's tissue at the cauterization site at a relatively high current density over a small area, and then passes through and out of the patient's body over a much larger surface area where the patient is contacted by a conductive surface connected to a terminal of an external electrical power source providing the requisite cauterization current.

Reference may be had at this point to FIG. 5 which schematically illustrates a patient 500 lying in electrically conductive contact on a surface of a large conductive pad 502 which is electrically connected by an electrical line 504 to, for example, the negative terminal of an electrical power source 506. Electrical conductive pad 502 is supported on the upper surface of an operating table 508 which may, preferably, be insulated from electrical power source 506 or be commonly grounded therewith. Through a user-operated and preferably foot-actuated switch 510, the positive terminal of electrical power source 506 may be connected to an electrical line 512 connected, as indicated in FIG. 2, to inner metal tubing 210. To ensure physical security of electrical line 512, it may be epoxied to the outer surface of outer tubing 216 at 514 and be electrically connected to the swaged portion of inner tubing 210 at 516.

By actuation of foot-control 510 and by contacting the external surface of conical portion 212 of inner tubing 210 to the patient's body, the surgeon-user can generate the needed cauterizing current at the point of contact. The surgeon-user can thus utilize another portion of the incision-making tip structure itself to cauterize blood vessels as these are incised, without having to depend on an assistant and without having to change tools.

Referring now to FIG. 3, there is seen another preferred embodiment which is a modified form of the embodiment according to FIG. 2. For simplicity, those portions of the structures of FIGS. 2 and 3 which are exactly the same in form and function are given the same reference numerals in FIG. 3 as in FIG. 2. The significant structural difference between the embodiments illustrated in FIGS. 2 and 3 is that in the latter, the inner tubing 210 is, in effect, cut in its cylindrical portion and is then connected to opposite sides of a short thermally and electrically insulating matchingly-sized cylinder 310. Cylinder 310 is preferably made of a high temperature ceramic material which can be molded, e.g., alumina. A suitable machinable alumina material is one commercially sold by Corning Corporation under the name "Macor" (TM). It is somewhat softer than conventional alumina and can be readily machined, and this is important because it is desirable to make the outer diameter of cylinder 310 the same as the outer diameter of inner tubing 210.

The purpose in thus including a thermally nonconductive element 310 is two-fold: first, it prevents excessive heat transfer away from the heated tip and thus makes it more efficient; and second, it helps in keeping outer tubing 216 cool.

The actual connection between cylinder 310 and inner tubing 210 which is swaged to a sealed pointed end 214 on one side and the cylindrical portion 210a (so numbered for ease of reference) is accomplished by the use of a high-temperature epoxy adhesive, e.g., one commercially available under the name "Epotex" (TM) identified by the numerals 250,250 in FIG. 3. It should be understood that cylinder 310, like inner metal tubing 210 is a hollow cylinder. It is not essential that the inner diameter of cylinder 310 be the same as the inner diameter of inner tubing 210 since no suction-inducted flow is conducted inside inner metal tubing 210. Cylinder 310 must, however, have an inside diameter larger than the outer diameter of cladding 204 on optical fiber 202.

The actual physical forming of the various vents, conical shapes, sealing of tip end 214 (e.g., by welding), and the actual assembly of the finished structure for either FIGS. 2 or 3, are all manufacturing details considered to be well within the purview of persons of ordinary skill in the art.

By either of the preferred embodiments described in the immediately preceding paragraphs, the surgeon-user is provided various facilities for selectively incising or cauterizing tissues while, simultaneously, removing any odors, smoke, and gas or vaporized substances generated during either surgical incision or cauterization. Specifically, in any known manner, e.g., by a hand-actuated switch on the surgical tool, the surgeon-user may apply a controlled flow of laser light energy to heat the pointed tip 214 to effect incisions. The application of suction to promote evacuation of the gaseous and/or vaporized substances, as previously described, can likewise be controlled by the surgeon-user or maintained continuously. Furthermore, by the structure illustrated in FIG. 5, the surgeon-user can cause a voltage difference to be applied between the conical portion 212 of the tip element and the body of the patient 500 at an inside blood vessel to thereby generate the required local high current density to cause electrocauterization. This occurs without unacceptable discomfort or harm to the patient since the current thus generated will leave the patient over a relatively large area of his or her body at a corresponding low current density.

In this manner, the surgeon can operate in a confined space in the patient's body, using a single tool and by combined actuation of a hand-operated switch controlling the flow of laser energy and the foot-operated switch 510 to control a cauterization current to proceed rapidly and efficiently. As will be readily understood, only the preferred embodiments are described with particular reference to FIGS. 2 and 3. Persons of ordinary skill in the art, seeking to extend the utility of the present invention, can be expected to consider other than the simple conical shape for the heated portion of the device. Such obvious modifications are considered to be comprehended within the exemplary descriptions provided herein.

In this disclosure, there are shown and described only the preferred embodiments of the invention, but, as aforementioned, it is to be understood that the invention is capable of use in various other combinations and environments and is capable of changes or modifications within the scope of the inventive concept as expressed herein.

What is claimed is:

1. A tip element for applying a high temperature energy flux, comprising:
   an optical fiber comprising a laser light transmitting first material, having an extended distal end portion formed into a conical shape with an end face for emitting laser energy therefrom; and
   a cover element comprising a second material, formed and positioned with respect to said distal end of the optical fiber so as to cover the same and thereby receive laser energy emitted therefrom, whereby a heat-applying first portion of said cover element is heated,
   wherein said heat-applying first portion of said cover element is formed as a closed cone, and said conically-shaped extended distal end portion of said optical fiber is correspondingly shaped and fitted to an inside surface of said cone.

2. The tip element according to claim 1, wherein:
   said cover element comprises a first cylindrical portion surrounding a length of said optical fiber for a predetermined length away from said conically-shaped portion and said laser energy emitting end face thereof.

3. The tip element according to claim 2, further comprising:
   a tubular element comprising a third material surrounding said cylindrical portion of said cover element, whereby an annular space is defined between an outer surface of said cylindrical portion of said cover element and an inside surface of said tubular element; and
   a perforated locating element comprising a fourth material supported inside said tubular element, having a first opening sized to closely receive said cylindrical portion of said cover element therethrough to support the same and having at least one flow opening to permit throughflow therethrough via said annular space.

4. The tip element according to claim 3, wherein:
   said first material comprises quartz.

5. The tip element according to claim 3, wherein:
   said second material comprises at least one of titanium and stainless steel.

6. The tip element according to claim 3, wherein:
   said third material comprises at least one of titanium and stainless steel.

7. The tip element according to claim 3, wherein:
   said fourth material is electrically non-conductive.

8. The tip element according to claim 7, wherein:
   said locating element comprises a ceramic material.

9. The tip element according to claim 3, further comprising:
   means for electrically connecting said cover element to an electrical terminal.

10. The tip element according to claim 9, further comprising:
    a user-operated means for controlling an electrical voltage at said electrical terminal.

11. The tip element according to claim 2, wherein:
    said cylindrical portion of said cover element comprises a first cylindrical portion formed of said second material, connected to a second cylindrical portion formed of a fifth material, and a third portion formed of said second material, said first, second and third portions being formed to have a substantially continuous outer cylindrical surface.

12. The tip element according to claim 11, wherein:
    said fifth material comprises a thermally and electrically insulating material.

13. The tip element according to claim 12, wherein:
    said second portion is connected to said first and third portions by a high-temperature adhesive material.

14. The tip element according to claim 13, wherein:
    said high-temperature adhesive material comprises an epoxy material.

15. The tip element according to claim 12, further comprising:
    a tubular element comprising a third material surrounding said cylindrical portion of said cover element, whereby an annular space is defined between an outer surface of said cylindrical portion of said cover element and an inside surface of said tubular element; and
    a perforated locating element supported inside said tubular element, having a first opening sized to closely receive said cylindrical portion of said cover element therethrough to support the same and having at least one flow opening to permit throughflow therethrough via said annular space.

16. The tip element according to claim 15, wherein:
    said first material comprises quartz.

17. The tip element according to claim 15, wherein:
    said second material comprises at least one of titanium and stainless steel.

18. The tip element according to claim 15, wherein:

said third material comprises at least one of titanium and stainless steel.

19. The tip element according to claim 18, wherein: said locating element comprises a ceramic material.

20. The tip element according to claim 15, further comprising:
means for electrically connecting said first portion of said cover element to an electrical terminal.

21. The tip element according to claim 20, further comprising:
a user-operated means for controlling an electrical voltage at said electrical terminal.

22. The tip element according to claim 3, further comprising:
means for applying a controlled suction to said annular space, to thereby enable a flow of ambient air and any vaporized or gaseous products away from said first portion of said cover element during use thereof to apply heat to tissue.

23. The tip element according to claim 10, further comprising:
means for applying a control suction to said annular space, to thereby enable a flow of ambient air and any vaporized or gaseous products away from said first portion of said cover element during use thereof to apply heat to tissue.

24. The tip element according to claim 15, further comprising:
means for applying a controlled suction to said annular space, to thereby enable a flow of ambient air and any vaporized or gaseous products away from said first portion of said cover element during use thereof to apply heat to tissue.

25. The tip element according to claim 20, further comprising:
means for applying a controlled suction to said annular space, to thereby enable a flow of ambient air and any vaporized or gaseous products away from said first portion of said cover element during use thereof to apply heat to tissue.

26.. The tip element according to claim 10, further comprising:
an electrically conductive object-supporting element formed to support an object by contacting the object over a large inner area to provide a predetermined low current density return path to an electrical current generated by a user-controlled electrical voltage applied to said object via said first portion of said cover element.

27. The tip element according to claim 21, further comprising:
an electrically conductive object-supporting element formed to support an object by contacting the object over a large inner area to provide a predetermined low current density return path to an electrical current generated by a user-controlled electrical voltage applied to said object via said first portion of said cover element.

28. A method for precisely applying to an object a controlled high temperature energy flux generated from laser energy conveyed along an optical fiber from a laser sources, comprising the steps of:
shaping a distal end portion of the optical fiber as a cone having a reduced end surface for emission of laser energy therefrom;
covering said conically-shaped distal end portion of said optical fiber with a thermally conducting cover element having a correspondingly shaped conical distal tip portion with an inside surface for receiving and absorbing laser energy emitted from said end surface of said optical fiber and converting the same to heat for heating said top portion of cover element to a high temperature; and
applying said heated tip portion to a selected location on said object for applying a high temperature energy flux thereat.

29.. The method according to claim 28, comprising the further step of:
applying a suction immediately adjacent and around the heated tip portion of said cover element, to thereby remove from said location of its application to said object any vaporized or gaseous products generated by the application of said high temperature energy flux thereat.

30. The method according to claim 28, comprising the further step of:
applying a controlled voltage difference between said object and said cover element, to thereby generate an electrical current by contacting said cover element to a selected location on said object.

31. The method according to claim 29, comprising the further step of:
applying a suction immediately adjacent and around the heated tip portion of said cover element, to thereby remove from said location of its application to said object any vaporized or gaseous products generated by the application of said high temperature energy flux thereat.

* * * * *